(12) United States Patent
Jeong et al.

(10) Patent No.: US 12,414,919 B2
(45) Date of Patent: Sep. 16, 2025

(54) METHOD FOR PREPARING BIOCOMPATIBLE POLYMER-BASED APIXABAN-LOADED MICROSPHERES

(71) Applicant: HLB PHARMACEUTICAL CO., LTD., Gyeonggi-do (KR)

(72) Inventors: Dooyong Jeong, Gyeonggi-do (KR); Sang-Hwi Lee, Gyeonggi-do (KR); Mijung Kim, Gyeonggi-do (KR); Ye-Ji Kim, Ulsan (KR); Jae Hyung Park, Seoul (KR)

(73) Assignee: HLB PHARMACEUTICAL CO., LTD. (KR)

( * ) Notice: Subject to any disclaimer, the term of this patent is extended or adjusted under 35 U.S.C. 154(b) by 952 days.

(21) Appl. No.: 17/598,495

(22) PCT Filed: Mar. 20, 2020

(86) PCT No.: PCT/KR2020/003885
§ 371 (c)(1),
(2) Date: Sep. 27, 2021

(87) PCT Pub. No.: WO2020/197190
PCT Pub. Date: Oct. 1, 2020

(65) Prior Publication Data
US 2022/0183978 A1    Jun. 16, 2022

(30) Foreign Application Priority Data
Mar. 27, 2019    (KR) .................. 10-2019-0035355

(51) Int. Cl.
*A61K 9/16* (2006.01)
*A61K 9/00* (2006.01)
*A61K 31/4545* (2006.01)

(52) U.S. Cl.
CPC .......... *A61K 9/1682* (2013.01); *A61K 9/0019* (2013.01); *A61K 9/1617* (2013.01); *A61K 31/4545* (2013.01)

(58) Field of Classification Search
CPC ...... A61K 9/16; A61K 9/1682; A61K 9/1694; A61K 31/4545
See application file for complete search history.

(56) References Cited

U.S. PATENT DOCUMENTS

| 5,250,236 A * | 10/1993 | Gasco ................. A61K 9/5123 |
|  |  | 264/4.4 |
| 2017/0202826 A1 | 7/2017 | Nause |
| 2022/0183976 A1* | 6/2022 | Jeong ................. A61K 9/1617 |

FOREIGN PATENT DOCUMENTS

| CN | 104523623 A | 4/2015 |
| KR | 20120029428 A | 3/2012 |
| KR | 102044676 B1 | 11/2019 |
| KR | 102045721 B1 | 11/2019 |
| WO | 2010147978 A1 | 12/2010 |

OTHER PUBLICATIONS

Jafarifar, E.; et al. "Preparation of a reproducible long-acting formulation of risperidone-loaded PLGA microspheres using microfluidic method" 2017, Pharmaceutical Development and Technology, vol. 22, p. 836-843. (Year: 2017).*
Technical Data Sheet for Miglyol® 812 N; published by IOI Oleochemical; revised Apr. 2017. (Year: 2017).*
Pubchem database entry for Stearic acid (Pubchem CID 5281); accessed Jul. 8, 2024. (Year: 2024).*
Dong, X.; et al. "Development of new lipid-based paclitaxel nanoparticles using sequential simplex optimization" 2009, European Journal of Pharmaceutics and Biopharmaceutics, vol. 72, pp. 9-17. (Year: 2009).*
Anwer, K.; et al. "Sustained release and enhanced oral bioavailability of rivaroxaban by PLGA nanoparticles with NO food effect" 2020, Journal of Thrombosis and Thrombolysis, vol. 49, pp. 404-412 (published online Jan. 2, 2020). (Year: 2020).*
Zhang, H.; et al. "Simultaneous determination of kolliphor HS15 and miglyol 812 in microemulsion formulation by ultra-high performance liquid chromatography coupled with nano quantity analyte detector" 2016, Journal of Pharmaceutical Analysis, vol. 6, pp. 11-17. (Year: 2016).*
Spenlehauer et al. "In vitro and in vivo degradation of poly( D,L lactide/glycolide) type microspheres made by solvent evaporation method", Biomaterials Oct. 1989, vol. 10, pp. 557-563.
Rivera et al. "Fluconazole encapsulation in PLGA microspheres by spray-drying". J. Microencapsulation Mar. 2004, vol. 21, No. 2, pp. 203-211.

(Continued)

*Primary Examiner* — Eric Olson
*Assistant Examiner* — Benjamin M Brandsen
(74) *Attorney, Agent, or Firm* — Dickinson Wright PLLC

(57) ABSTRACT

The present disclosure relates to a method for preparing biocompatible polymer-based Apixaban-loaded microspheres. More specifically, the present disclosure relates to a method for preparing biocompatible polymer-based Apixaban-loaded microspheres, where the method includes: i) adding a fatty acid or triglyceride to a dispersed phase; and ii) preparing microspheres using a microfluidic method. The method for preparing biocompatible polymer-based Apixaban-loaded microspheres of the present disclosure may be effectively used in the preparation of microspheres in which Apixaban is stably encapsulated in high contents.

5 Claims, 7 Drawing Sheets

(56) References Cited

OTHER PUBLICATIONS

Sah, "Microencapsulation techniques using ethyl acetate as a dispersed solvent: effects of its extraction rate on the characteristics of PLGA microspheres", Journal of Controlled Release 1997, vol. 47, No. 3, pp. 233-245.
Ryu et al. "Sustained release of antibiotics from uniform poly (ε-caprolactone) microspheres prepared by a simple luidic device with a tapered glass capillary", Journal of Bioactive and Compatible Polymers 2014, vol. 29, No. 4, pp. 318-329.
Rezvantalab et al. "Microfluidic assisted synthesis of PLGA drug delivery systems", RSC Adv., 2019, vol. 9, pp. 2055-2072.
Chu et al. "Poly(Lactic-co-glycolic Acid) Microspheres for the Controlled Release of Huperzine A: In Vitro and in Vivo Studies and the Application in the Treatment of the Impaired Memory of Mice", Chem. Pharm. Bull. 2007, vol. 55, No. 4, pp. 625-628.

\* cited by examiner

[Fig. 1]
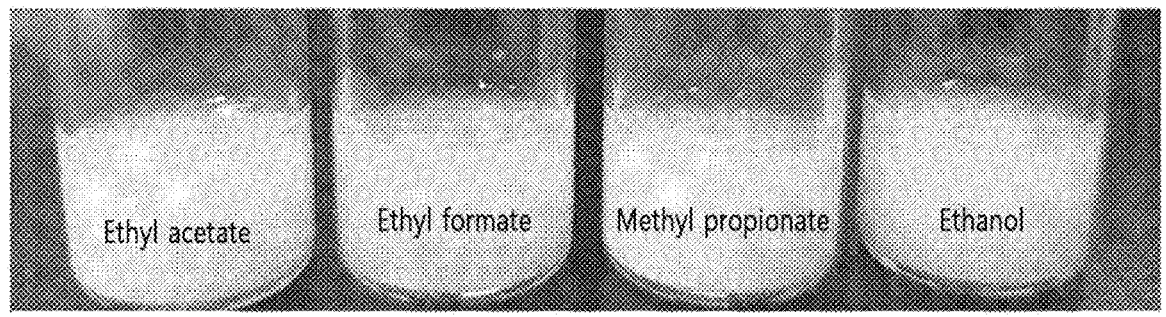
[Fig. 2]
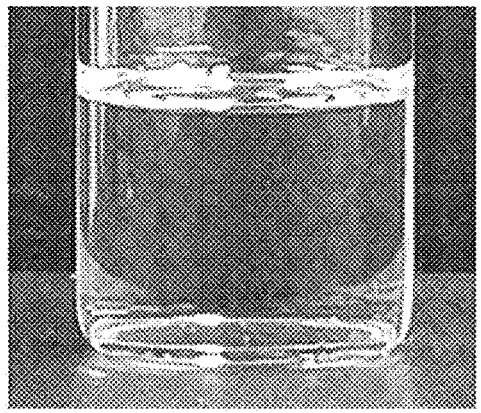 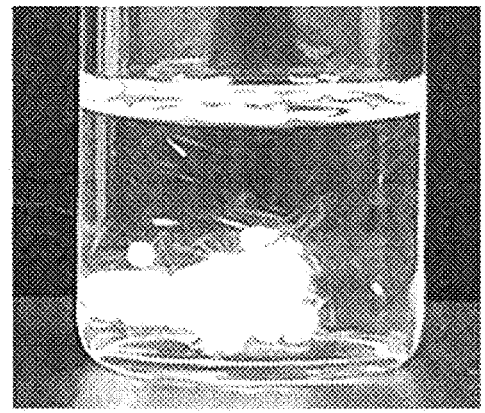

[Fig. 3]
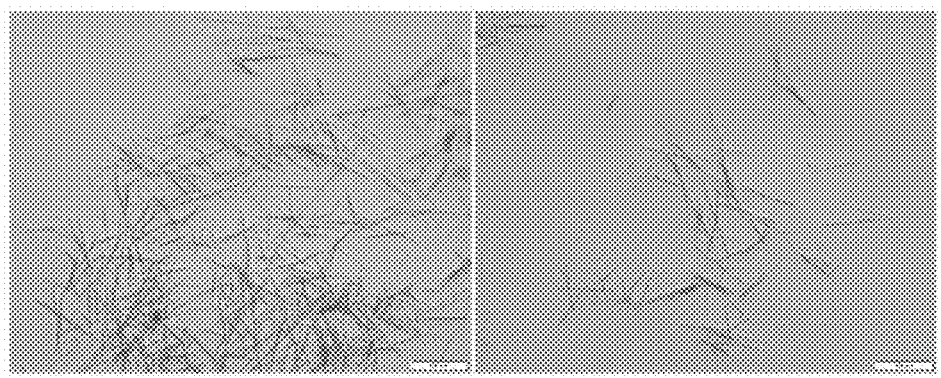
[Fig. 4]
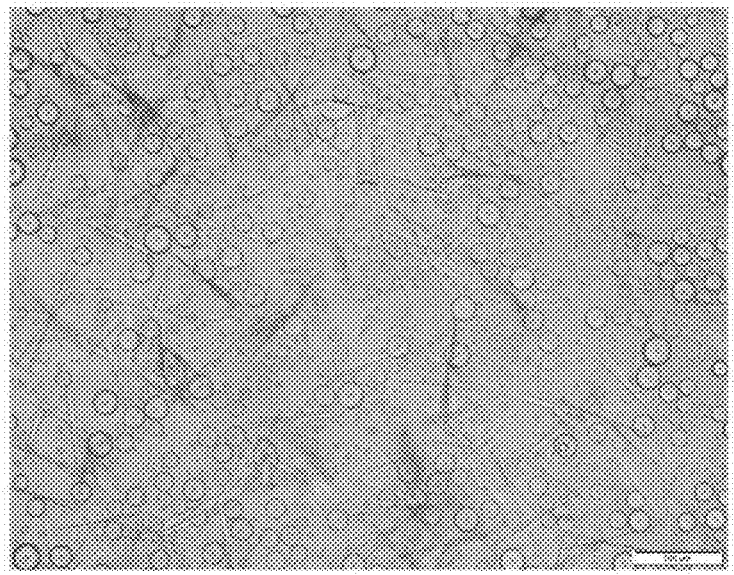

[Fig. 5]
[Fig. 6]

[Fig. 7]
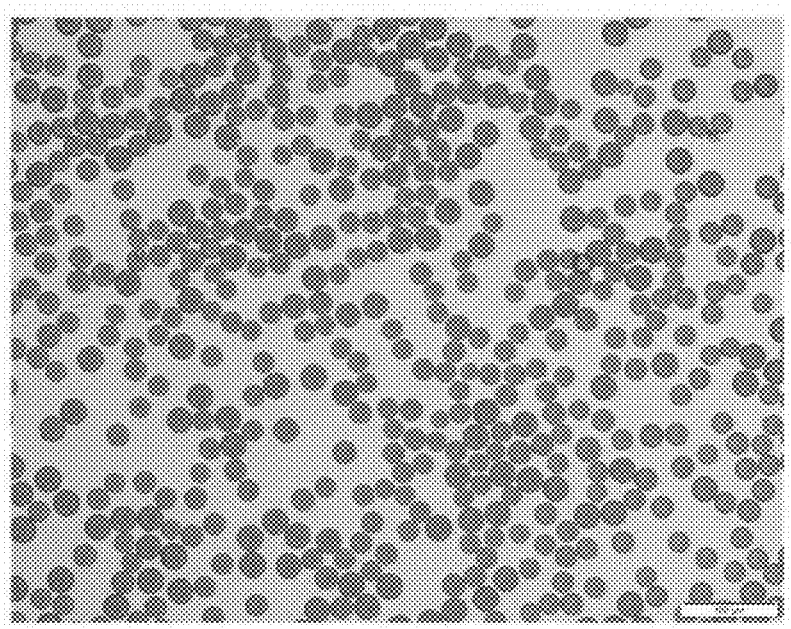
[Fig. 8]
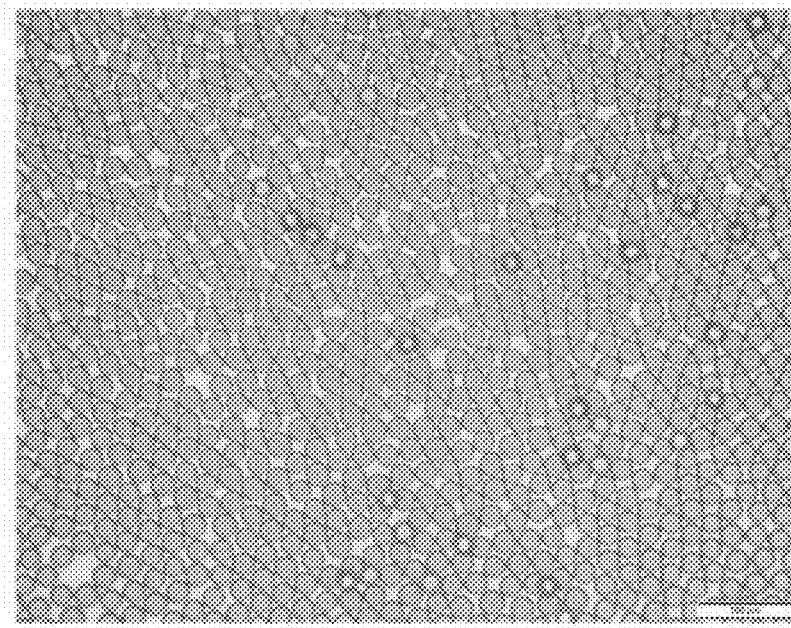

[Fig. 9]
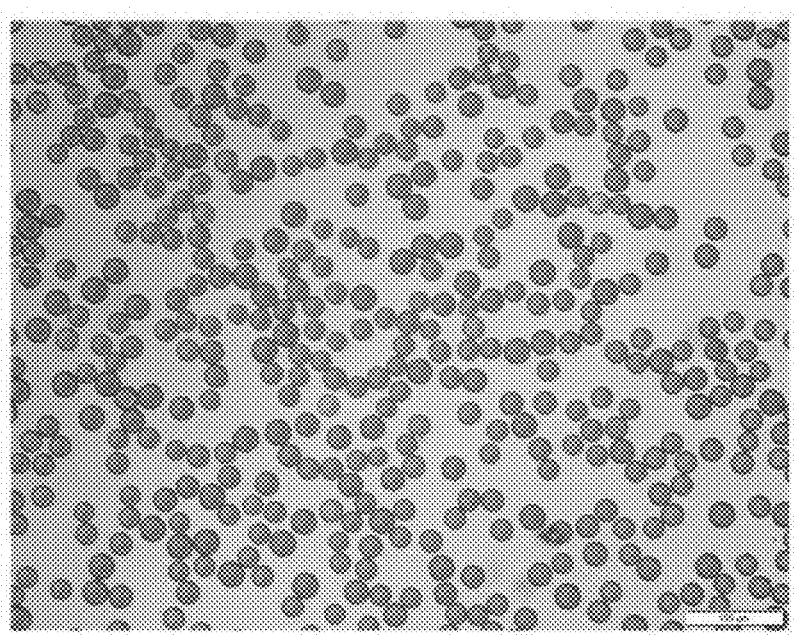
[Fig. 10]
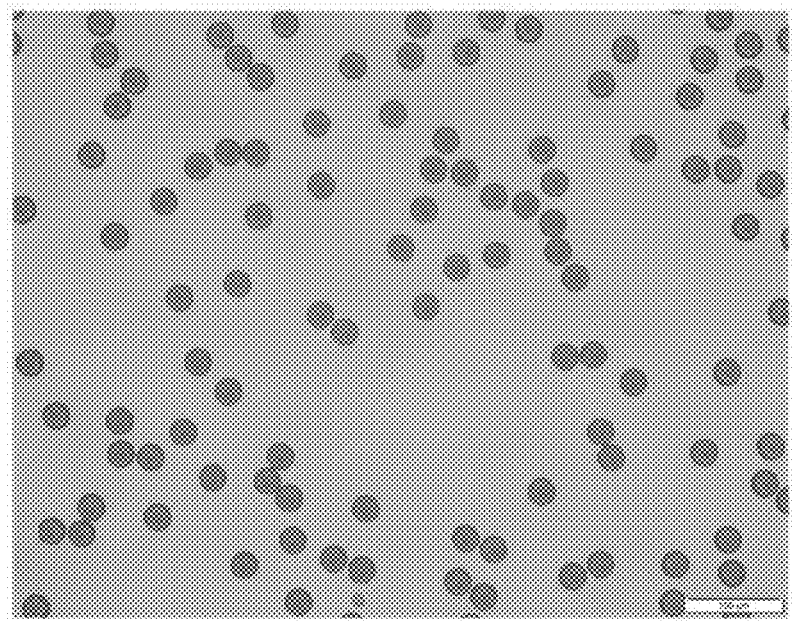

[Fig. 11]
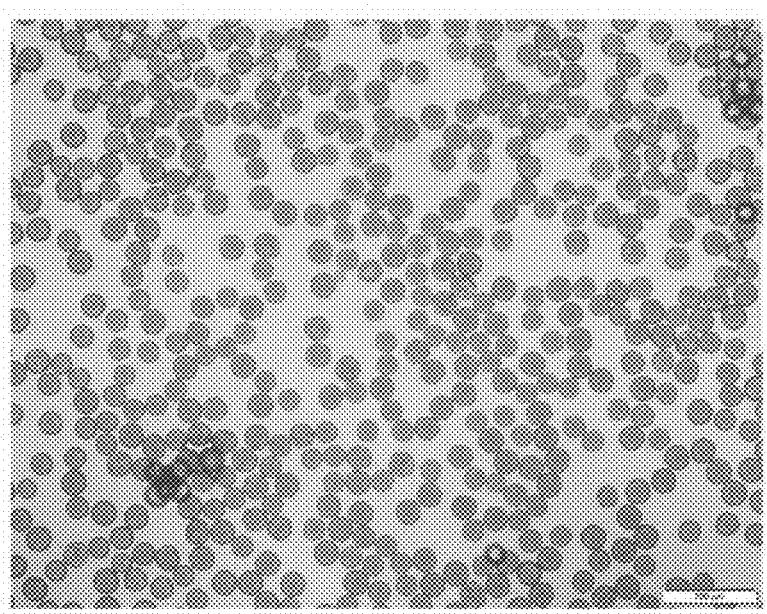
[Fig. 12]
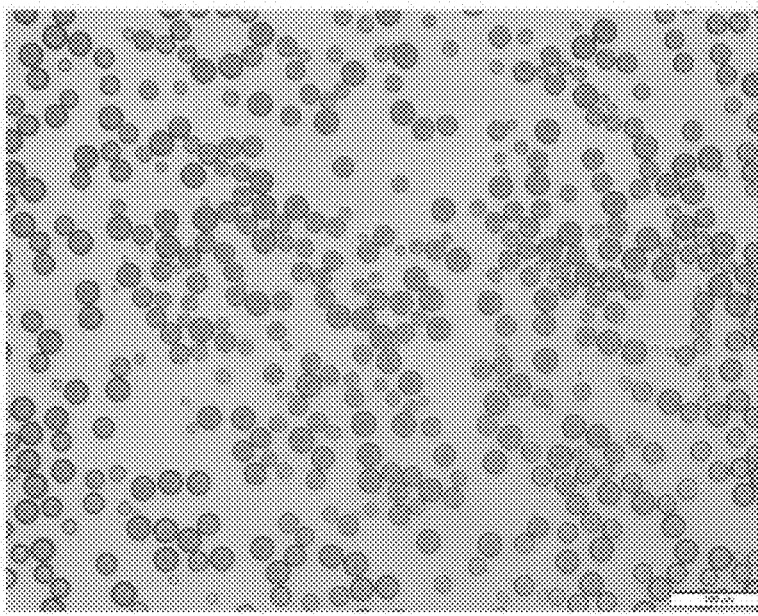

[Fig. 13]
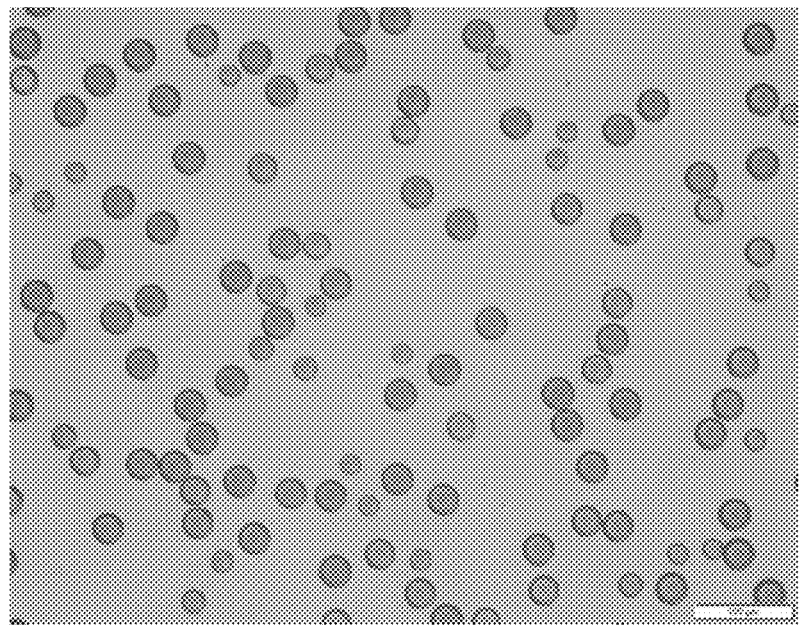

METHOD FOR PREPARING BIOCOMPATIBLE POLYMER-BASED APIXABAN-LOADED MICROSPHERES

CROSS-REFERENCE TO RELATED APPLICATIONS

This application is the U.S. National Phase of PCT/KR2020/003885 filed Mar. 20, 2020, which claims priority to KR 10-2019-0035355 filed Mar. 27, 2019, the entire disclosures of which are incorporated by reference herein.

TECHNICAL FIELD

The present disclosure relates to a method for preparing biocompatible polymer-based Apixaban-loaded microspheres. More specifically, the present disclosure relates to a method for preparing biocompatible polymer-based Apixaban-loaded microspheres, including: i) adding a fatty acid or triglyceride to a dispersed phase; and ii) preparing microspheres using a microfluidic method.

BACKGROUND

Apixaban is a drug that prevents the formation of blood clots and blood coagulation by selectively inhibiting the coagulation factor Xa in the blood coagulation step. Apixaban is administered orally for the purpose of preventing venous thromboembolism in adult patients who have had a hip or knee replacement, reducing the risk of stroke and systemic embolism in patients with nonvalvular atrial fibrillation, and treating deep vein thrombosis and pulmonary embolism and reducing the risk of recurrence thereof.

However, when Apixaban is orally administered, the absorption in the body is inhibited by a low water solubility of Apixaban, and accordingly, it is known to exhibit about 50% bioavailability. Additionally, with respect to Apixaban, which is one of the orally administered non-vitamin K antagonist oral anticoagulants (NOAC), gastrointestinal bleeding may be caused by a combined mechanism of 1) systemic anticoagulant effects, 2) local anticoagulant effects, 3) local direct corrosive actions, and 4) non-coagulation-related local biological actions, etc., or after oral administration, Apixaban exists in an active form in the intestinal tract in order to play a role in anticoagulation, which may lead to bleeding in various lesions in the intestinal tract. Accordingly, there is a need for a novel administration route to overcome the low bioavailability of Apixaban and to reduce gastrointestinal bleeding.

With respect to looking for a novel administration route for the existing orally administered drugs, biocompatible polymer-based microspheres have advantages in that, since they are typically formulated into an injection for intramuscular or subcutaneous administration, a drug can be encapsulated therein, and also, the microspheres are gradually and completely degraded after injection in vivo, thereby releasing the drug by 100%, and thus, the in vivo effective concentration of the drug can be maintained for a long time.

Accordingly, in the case of encapsulating Apixaban into the biocompatible polymer-based microspheres, the administration route of Apixaban can be altered to an injection for intramuscular or subcutaneous administration from the conventional oral administration, and thus, it is expected to improve the bioavailability.

The known preparation methods for microspheres include i) a solvent evaporation method, ii) a spray drying method, iii) a solvent extraction method, iv) a microfluidic method (Biomaterials, 1989, 10(8) 557-563; Journal of microencapsulation, 2004, 21(2) 203-211; Journal of Controlled Release, 1997, 47(3) 233-245; Journal of Bioactive and Compatible Polymers, 2014, 29(4) 318-329). However, Apixaban has never been developed as a microsphere formulation using the preparation methods above. In addition, the methods for preparing Apixaban-loaded microspheres are also not known to date.

SUMMARY

Technical Problem

The present inventors have made extensive effects to develop a method for preparing biocompatible polymer-based Apixaban-loaded microspheres, and as a result, they have confirmed that when microspheres are prepared by adding a fatty acid or triglyceride to a dispersed phase and using a microfluidic method, microspheres in which Apixaban is stably encapsulated in high contents can be prepared, thereby completing the present disclosure.

Technical Solution

An object of the present disclosure is to provide a method for preparing biocompatible polymer-based Apixaban-loaded microspheres, including:

i) adding a fatty acid or triglyceride to a dispersed phase; and ii) preparing microspheres using a microfluidic method.

Advantageous Effects

The method for preparing biocompatible polymer-based Apixaban-loaded microspheres of the present disclosure can be effectively used for the preparation of microspheres in which high contents of Apixaban is stably encapsulated.

BRIEF DESCRIPTION OF THE DRAWINGS

FIG. 1 is an image taken with a digital camera after adding Apixaban to each of ethyl acetate, ethyl formate, methyl propionate, and ethanol, which are non-halogen organic solvents, followed by stirring.

FIG. 2 shows images taken with a digital camera immediately and 12 hours after dissolving Apixaban in dichloromethane.

FIG. 3 shows optical microscopic images of crystals formed 12 hours after dissolving Apixaban in dichloromethane.

FIG. 4 is an optical microscopic image of polymer-based Apixaban-loaded microspheres (Comparative Example 1) prepared in Experimental Example 3-1.

FIG. 5 is an optical microscopic image of polymer-based Apixaban-loaded microspheres (Comparative Example 2) prepared in Experimental Example 3-2.

FIG. 6 is an optical microscopic image of polymer-based Apixaban-loaded microspheres (Comparative Example 3) prepared in Experimental Example 4.

FIG. 7 is an optical microscopic image of polymer-based Apixaban-loaded microspheres (Example 1) prepared in Experimental Example 5-1.

FIG. 8 is an optical microscopic image of polymer-based Apixaban-loaded microspheres (Example 2) prepared in Experimental Example 5-2.

FIG. 9 is an optical microscopic image of polymer-based Apixaban-loaded microspheres (Example 3) prepared in Experimental Example 5-3.

FIG. 10 is an optical microscopic image of polymer-based Apixaban-loaded microspheres (Example 4) prepared in Experimental Example 5-4.

FIG. 11 is an optical microscopic image of polymer-based Apixaban-loaded microspheres (Example 5) prepared in Experimental Example 5-5.

FIG. 12 is an optical microscopic image of polymer-based Apixaban-loaded microspheres (Example 6) prepared in Experimental Example 5-6.

FIG. 13 is an optical microscopic image of polymer-based Apixaban-loaded microspheres (Example 7) prepared in Experimental Example 5-7.

DETAILED DESCRIPTION

In order to achieve the objects, one aspect of the present disclosure invention provides a method for preparing biocompatible polymer-based Apixaban-loaded microspheres, including: i) adding a fatty acid or triglyceride to a dispersed phase; and ii) preparing microspheres using a microfluidic method.

Specifically, one aspect of the present disclosure may provide a method for preparing biocompatible polymer-based Apixaban-loaded microspheres in the form of an injection for sustained release, including the steps above.

As used herein, the term "Apixaban" refers to a compound which has the structure of Chemical Formula 1. Apixaban has three amides in the structure and has an intrinsic dipole structure of the amides. Thus, Apixaban can form intermolecular hydrogen bonds composed of N—H . . . O, and thus can form co-precipitates in a suitable solvent when a proton donor or a proton accepter is present, or can also form intermolecular hydrogen bonds between Apixaban molecules. Accordingly, even when only Apixaban is dissolved, crystals may be formed after a certain period of time.

[Chemical Formula 1]

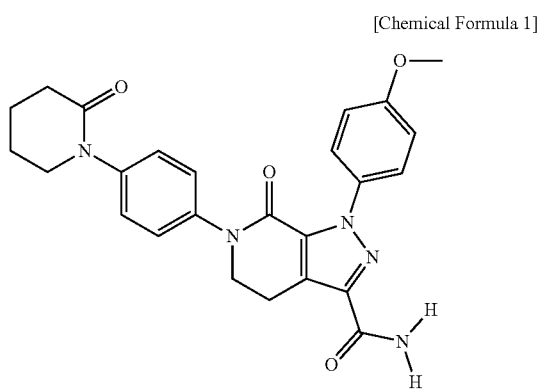 [SMILES: COc1ccc(-n2nc(C(N)=O)c3c2C(=O)N(c2ccc(N4CCCCC4=O)cc2)CC3)cc1]

Since such phenomenon of drug crystallization significantly reduces the content of the drug in the microspheres and since there is no way to completely remove the drug crystals produced during the preparation of the microspheres from the microspheres in which the drug is encapsulated, it is necessary to prevent drug crystal formation during the preparation of the microspheres.

Hydrophobic drugs such as Apixaban generally have a tendency that they are precipitated during the preparation of microspheres to form crystals. In this case, the precipitation of crystals may be prevented by using a high concentration/ high viscosity polymer solution, reducing the amount of drug added, changing the type of organic solvent, or reducing the volatilization temperature of the solvent. These methods are applied to reduce the probability of contact between the drug and water and to control the rate at which the polymer cures, thereby allowing the drug to be physically encapsulated in the microspheres.

In consideration of the recommended daily dose of Apixaban and the total duration of drug release from the microspheres, the criteria of high drug content in the microspheres should be taken into account for the development of microspheres for sustained-release of Apixaban. Therefore, it would be difficult to apply the method of significantly reducing the drug content in the microspheres, reducing the amount of drug added, or using a high concentration polymer solution to the preparation of biocompatible polymer-based Apixaban-loaded microspheres.

Additionally, the method of changing the type of organic solvent or reducing the solvent evaporation temperature in manufacturing process may not be suitable for application in the preparation of the Apixaban-loaded microspheres, because the solubility of Apixaban in most of volatile non-halogen organic solvents is extremely limited, and there is a problem of a residual solvent with respect to the complete removal of the solvent.

Accordingly, Apixaban has never been developed as microspheres to date, nor have the preparation methods of Apixaban-loaded microspheres been known. In this regard, it is significantly meaningful from the viewpoint that the method for preparing biocompatible polymer-based Apixaban-loaded microspheres has been developed for the first time by the present inventors.

In the present disclosure, the Apixaban may include a pharmaceutically acceptable salt thereof.

As used herein, the term "pharmaceutically acceptable salt" refers to a salt in the form that can be pharmaceutically used, among the salts, which are the substances having cations and anions coupled by electrostatic attraction. Typically, it may include metal salts, organic base salts, inorganic acid salts, organic acid salts, basic or acidic amino acid salts, etc. Examples of the metal salts may include alkali metal salts (sodium salts, potassium salts, etc.), alkaline earth metal salts (calcium salts, magnesium salts, barium salts, etc.), or aluminum salts; examples of the organic base salts may include triethylamine, pyridine, picoline, 2,6-lutidine, ethanolamine, diethanolamine, triethanolamine, cyclohexylamine, dicyclohexylamine, N,N'-dibenzyl ethylenediamine, etc.; examples of the inorganic acid salts may include hydrochloric acid, hydrobromic acid, nitric acid, sulfuric acid, phosphoric acid, etc.; examples of the organic acid salts may include formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, etc.; examples of the basic amino acid salts may include arginine, lysine, ornithine, etc.; and examples of the acidic amino acid salts include aspartic acid, glutamic acid, etc.

As used herein, the term "biocompatible polymer-based Apixaban-loaded microsphere" refers to a microsphere, in which Apixaban is encapsulated, which is prepared using a biocompatible polymer, and may be also simply referred to as Apixaban-loaded microspheres, Apixaban microspheres, or microspheres. The microsphere is not limited by the type of polymers, and any microsphere falls within the scope of the present disclosure as long as Apixaban can be encapsulated in the microsphere, which is prepared using a biocompatible polymer.

Additionally, the biocompatible polymer-based Apixaban-loaded microspheres may be for sustained release of Apixaban, and may be formulated into an injection for subcutaneous or intramuscular administration. As used herein, the term "sustained release" refers to releasing the drug for a long time in vivo by controlling the release mechanism of the drug. Specifically, in the present disclosure, it may refer to the inhibition of the initial drug release, but is not limited thereto.

In this regard, the biocompatible polymer-based Apixaban-loaded microspheres prepared in the present disclosure may specifically be biocompatible polymer-based Apixaban-loaded microspheres in the form of an injection for sustained release.

The method of the present disclosure for preparing biocompatible polymer-based Apixaban-loaded microspheres includes adding a fatty acid or triglyceride into a dispersed phase.

In the present disclosure, the fatty acid or triglyceride can be used without limitation as long as it i) is pharmaceutically acceptable, ii) has a functional group capable of forming a hydrogen bond with Apixaban, iii) shows a high solubility in a halogen organic solvent, while having no impact on the effect of the present disclosure.

Additionally, the fatty acid or triglyceride may play a role in inhibiting the formation of Apixaban drug crystals.

As used herein, the term "fatty acid" refers to a compound having a saturated or unsaturated aliphatic chain and refers to a compound having at least one carboxyl group. The fatty acid can be used in the present disclosure because it i) is pharmaceutically acceptable, ii) has a carboxyl group capable of forming a hydrogen bond with Apixaban, iii) shows a high solubility in a halogen organic solvent. Specifically, the fatty acid may be a C12-18 fatty acid having one or more carboxyl groups with a melting point of 35° C. or higher, which is minimum temperature for evaporating an organic solvent when preparing microspheres, more specifically, it may be stearic acid, palmitic acid, or lauric acid, and even more specifically stearic acid or lauric acid, but is not limited thereto.

As used herein, the term "triglyceride" refers to a compound formed with three fatty acids and glycerol via an ester bond. The triglyceride can be used in the present disclosure because it i) is pharmaceutically acceptable; ii) has an ester group capable of forming a hydrogen bond with Apixaban, iii) shows a high solubility in a halogen organic solvent. Specifically, the triglyceride may be one formed with three fatty acids having at least 10 carbon atoms, which is in a solid form at room temperature, and glycerol via an ester bond, and more specifically, it may be glyceryl tridecanoate, glyceryl triundecanoate, glyceryl tridodecanoate, glyceryl trimyristate, glyceryl tripalmitate, or glyceryl tristearate. More specifically, it may be glyceryl tridodecanoate having a melting point of 35° C. or higher, which is a minimum temperature for evaporating an organic solvent when preparing microspheres, but is not limited thereto.

In one specific embodiment of the present disclosure; it was confirmed that when Apixaban-loaded microspheres were prepared using a general dispersed phase, to which no fatty acids or triglycerides were added, the microspheres could not be prepared as Apixaban rapidly precipitated into the aqueous phase to form needle-like crystals (FIGS. 4 and 5).

As used herein, the term "dispersed phase" refers to a composition for constituting an inner water phase in the case of microspheres in a water-in-oil phase, a composition for constituting an inner oil phase in the case of microspheres in an oil-in-water phase, and a composition for constituting a water-in-oil emulsion or primary emulsion in the case of microspheres in a water-in-oil-in-water phase, and thus refers to an inner phase excluding the outer phase of the composition for the preparation of microspheres, i.e., a mixture in the form in which a drug and a polymer are dissolved or dispersed.

In the present disclosure, the dispersed phase may include a biocompatible polymer and a halogen organic solvent.

As used herein, the term "biocompatible polymer" refers to a polymer whose in vivo safety has been ensured and which does not cause high cytotoxicity and inflammatory responses when administered in vivo, and it is also simply referred to herein as a polymer.

The biocompatible polymer used in the present disclosure may be specifically polyester, and more specifically, the polyester may be any one or more selected from the group consisting of polylactic-co-glycolic acid (PLGA), polylactic acid (PLA), and polycaprolactone (PCL), but is not limited thereto.

As used herein, the term "halogen organic solvent" refers to an organic solvent containing a halogen group element, such as F, Cl, Br, or I. In the case of Apixaban, unlike other common hydrophobic drugs, Apixaban has a low solubility in non-halogen organic solvents, and accordingly, non-halogen organic solvents cannot be used for the preparation of Apixaban microspheres.

In the present disclosure, the halogen organic solvent can be used for the preparation of microspheres as long as it does not have an impact on the effect of the present disclosure and is not limited by its type. Specifically, the halogen organic solvent may be dichloromethane (CH2C12), chloroform (CHCl3), carbon tetrachloride (CC14), and more specifically may be dichloromethane, but is not limited thereto.

In one specific embodiment of the present disclosure, Apixaban was not dissolved in non-halogen organic solvents, such as ethyl acetate, ethyl formate, methyl propionate, and ethanol, thereby confirming that the non-halogen organic solvents cannot be used for the preparation of Apixaban-loaded microspheres (FIG. 1). In contrast, Apixaban was temporarily dissolved in dichloromethane, a halogen organic solvent, confirming that the halogen organic solvent should be used for the preparation of Apixaban-loaded microspheres (FIGS. 2 and 3).

In the present disclosure, the dispersed phase may contain Apixaban or a pharmaceutically acceptable salt thereof in an amount of 10% to 50% by weight relative to the biocompatible polymer, but is not limited thereto.

If Apixaban or a pharmaceutically acceptable salt thereof is contained in an amount less than 10% by weight relative to the biocompatible polymer, a small amount of Apixaban is contained in the finally obtained microspheres, increasing the amount of microspheres to be administered in in vivo, and thus, it may be difficult to be used clinically. In contrast, if Apixaban or a pharmaceutically acceptable salt thereof is contained in an amount greater than 50% by weight relative to the biocompatible polymer, it may not be possible to inhibit the initial burst release of Apixaban from the microspheres.

In the present disclosure, the dispersed phase may contain the fatty acid or triglyceride in an amount of 50% by weight or less relative to the biocompatible polymer, but is not limited thereto.

If the fatty acid or triglyceride is contained in an amount greater than 50% by weight relative to the biocompatible polymer, the hardness of the microspheres may be reduced upon preparation of the microsphere, so that non-spherical particles may be prepared. The decrease in hardness and irregularity in shape of the microspheres may cause quality problems such as a decrease in physicochemical stability and a change in drug release rate.

In the present disclosure, the dispersed phase may contain the biocompatible polymer in an amount of 5 w/v % to 30 w/v % relative to the halogen organic solvent, but is not limited thereto.

If the biocompatible polymer is contained in an amount less than 5 w/v % relative to the halogen organic solvent, and the microfluidic method is used as an example of a preparation method for microspheres, the injection time may be prolonged as the volume of the composition increases in order to use the same amount of the polymer. Also, the low drug encapsulation efficiency and the inefficient solvent removing could be occurred due to the reduced viscosity of the dispersed phase. In contrast, if the biocompatible polymer is contained in an amount greater than 30 w/v % relative to the halogen organic solvent, the viscosity may become exceedingly high, thereby imposing constraints on the preparation of microspheres.

The method for preparing biocompatible polymer-based Apixaban-loaded microspheres includes preparing microspheres using a microfluidic method.

The present inventors have confirmed whether Apixaban-loaded microspheres can be prepared using a solvent evaporation method, a spray drying method, a solvent extraction method, and a microfluidic method, which are known preparation methods of microspheres.

In one specific embodiment of the present disclosure, it was confirmed that the solubility of Apixaban in ethyl acetate, ethyl formate, methyl propionate, and ethanol, which are non-halogen organic solvents, was very low (FIG. 1), while the solubility of Apixaban in dichloromethane, a halogen organic solvent, was very high (FIGS. 2 and 3).

It was found that from these results that Apixaban-loaded microspheres could not be prepared by the spray drying method and the solvent extraction, which mainly use the non-halogen organic solvents in the preparation of microspheres, and that Apixaban-containing microspheres should be prepared by the solvent evaporation method or the microfluidic method, which mainly uses the halogen organic solvent in the preparation of microspheres.

In one specific embodiment of the present disclosure, when Apixaban-loaded microspheres were prepared using a general dispersed phase in which no fatty acids or triglycerides have been added, it was observed that Apixaban rapidly precipitated into the aqueous phase to form needle-like crystals simultaneously with the start of the aqueous phase dispersion of liquid drops (oil phase) formed from the dispersed phase in both the solvent evaporation method and the microfluidic method (FIGS. 4 and 5).

From these results, it was found that the biocompatible polymer-based Apixaban-loaded microspheres could not be prepared using the general dispersed phase and the solvent evaporation method, and the general dispersed phase and the microfluidic method.

In one specific embodiment of the present disclosure, when Apixaban-loaded microspheres were prepared using a dispersed phase, to which fatty acids or triglycerides were added, by the solvent evaporation method, it was observed that Apixaban rapidly precipitated into the aqueous phase to form needle-like crystals simultaneously with the start of the dispersion (FIG. 6).

It was found from these results that the biocompatible polymer-based Apixaban-loaded microspheres could not be prepared by the solvent evaporation method even when the fatty acids or triglycerides were added.

In one specific embodiment of the present disclosure, when Apixaban-loaded microspheres were prepared using a dispersed phase, to which fatty acids or triglycerides were added, by the microfluidic method, it was found that the biocompatible polymer-based Apixaban-containing microspheres could be obtained, and drug precipitation was not observed.

It was found from these results that the biocompatible polymer-based Apixaban-loaded microspheres could only be prepared when the fatty acids or triglycerides were added to the dispersed phase and the microfluidic method was used.

The biocompatible polymer-based Apixaban-loaded microspheres of the present disclosure may contain Apixaban in an amount of 5% to 30% by weight. Specifically, it may contain Apixaban in an amount of 5% to 30% by weight, 8% to 28% by weight, 10% to 25% by weight, 12% to 22% by weight, and more specifically 15% to 20% by weight, but the amount is not limited thereto.

In one specific embodiment of the present disclosure, it was confirmed that the microspheres of Examples 1 to 6 provided by the present disclosure contained Apixaban in high contents in an amount of 15% to 20% by weight (Table 2).

In the present disclosure, the specific conditions of the microfluidic method, for example, the injection flow rate of the dispersed phase and the continuous phase, the stirring speed, the type of the solution used as the aqueous phase, etc. can be appropriately selected by those skilled in the art, and any specific conditions may be included within the scope of the present disclosure without limitation as long as Apixaban-loaded microspheres can be prepared.

The method of the present disclosure for preparing biocompatible polymer-based Apixaban-loaded microspheres may further include a general washing and drying process of microspheres after preparing the microspheres by the microfluidic method. Specifically, the method may further include filtering the prepared microspheres and washing with water, and freeze-drying or vacuum-drying the washed microspheres, but is not limited thereto.

Another aspect of the present disclosure provides biocompatible polymer-based Apixaban-loaded microspheres prepared by the preparation method above.

Mode for Carrying Out the Present Disclosure

The present disclosure will be described in more detail by way of Examples. However, these Examples are given for illustrative purposes only, and the scope of the disclosure is not intended to be limited to or by these Examples.

Experimental Example 1. Dissolution of Apixaban in Non-Halogen Organic Solvents 25 mg of Apixaban was added to 1 mL of each of ethyl acetate, ethyl formate, methyl propionate, and ethanol and stirred. As a result, it was confirmed that Apixaban was not dissolved in the four organic solvents (FIG. 1).

From these results, it was found that the solubility of Apixaban in the non-halogen organic solvents was very low, and thus, the Apixaban-loaded microspheres could not be prepared by the spray drying method and the solvent extraction method, which mainly use the non-halogen solvents in the preparation of the microspheres.

Experimental Example 2. Dissolution of Apixaban in Halogen Organic Solvent 25 mg of Apixaban was dissolved in 1 mL, of dichloromethane, and the mixture was photographed after 12 hours. As a result, it was found that Apixaban crystals were formed in dichloromethane (FIG. 2).

Additionally, the crystals were observed under an optical microscope, and as a result, it was found that needle-like structures were formed (FIG. 3).

From these results, it was found that even if Apixaban was temporarily dissolved in dichloromethane, it was recrystallized in the solvent over time due to a high crystallinity of Apixaban.

Experimental Example 3. Preparation of Apixaban-Loaded Microspheres Using General Dispersed Phase

Experimental Example 3-1. Preparation of Apixaban-Loaded Microspheres Using Solvent Evaporation Method (Comparative Example 1)

A dispersed phase was prepared by simultaneously dissolving 25 mg of Apixaban and 100 mg of PLA R202H in 1 mL of dichloromethane, and then the resultant was dispersed in a 1% poly vinyl alcohol (PVA) solution using a high shear mixer (Silverson, L5M-A), which was stirred at 1,500 rpm. In particular, Apixaban rapidly precipitated into the aqueous phase to form needle-like crystals simultaneously with the start of the dispersion (FIG. 4).

From these results, it was found that when the general dispersed phase and the solvent evaporation were used, Apixaban-loaded microspheres could not be prepared.

Experimental Example 3-2. Preparation of Apixaban-Loaded Microspheres using Microfluidic Method (Comparative Example 2)

A dispersed phase was prepared by simultaneously dissolving 25 mg of Apixaban and 100 mg of PLA R202H in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chip were obtained in the 1% PVA solution, which was stirred at 150 rpm. Subsequently, the thus-obtained microsphere liquid drops were observed under an optical microscope; and as a result, it was confirmed that needle-like crystals were formed in large amounts (FIG. 5).

From these results, it was found that when the general dispersed phase and the microfluidic method were used, Apixaban-loaded microspheres could not be prepared.

In order to separate the microspheres from the drug crystals as much as possible, the mixture was washed three times with pure water using a 75 μm mesh sieve. The separated microspheres were re-obtained using a membrane filter, followed by freeze-drying for 2 days to obtain dried microspheres.

Experimental Example 4. Preparation of Apixaban-Loaded Microspheres Using Solvent Evaporation Method (Comparative Example 3)

A dispersed phase was prepared by simultaneously dissolving 25 mg of Apixaban, 100 mg of PLA R202H, and 25 mg of stearic acid in 1 mL of dichloromethane, and then the resultant was dispersed in a 1% poly vinyl alcohol (PVA) solution using a high shear mixer (Silverson, LSM-A), which was stirred at 1,500 rpm. In particular, Apixaban rapidly precipitated into the aqueous phase to form needle-like crystals simultaneously with the start of the dispersion (FIG. 6).

From these results, it was found that even when the fatty acid or triglyceride was added to the dispersed phase, Apixaban-loaded microspheres could not be prepared by the solvent evaporation method.

Experimental Example 5. Preparation of Apixaban-Loaded Microspheres Using the Preparation Method of the Present Disclosure

Experimental Example 5-1. Preparation of Apixaban-Loaded Microspheres

Example 1

A dispersed phase was prepared by simultaneously dissolving 25 mg of Apixaban, 100 mg of PLA R202H, and 25 mg of stearic acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 7).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres

Experimental Example 5-2. Preparation of Apixaban-Loaded Microspheres (Example 2)

A dispersed phase was prepared by simultaneously dissolving 25 mg of Apixaban, 100 mg of PLGA RG75311, and 25 mg of stearic acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 8).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

Experimental Example 5-3. Preparation of Apixaban-Loaded Microspheres (Example 3)

A dispersed phase was prepared by simultaneously dissolving 25 mg of Apixaban, 100 mg of PLGA RC503H, and 25 mg of stearic acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 9).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

Experimental Example 5-4. Preparation of Apixaban-Loaded Microspheres (Example 4)

A dispersed phase was prepared by simultaneously dissolving 25 mg of Apixaban, 100 mg of PLGA RG5031-1, and 25 mg of lauric acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 10).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

Experimental Example 5-5. Preparation of Apixaban-Loaded Microspheres (Example 5)

A dispersed phase was prepared by simultaneously dissolving 25 mg of Apixaban, 90 mg of PLGA RC1753H, 10 mg of PCL (average molecular weight of 45,000 g/mol), and 25 mg of stearic acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 11).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

Experimental Example 5-6. Preparation of Apixaban Loaded Microspheres (Example 6)

A dispersed phase was prepared by simultaneously dissolving 25 mg of Apixaban, 90 mg of PLGA RG-75311, 10 mg of PLA R202H, and 25 mg of stearic acid in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 12).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

Experimental Example 5-7. Preparation of Apixaban Loaded Microspheres (Example 7)

A dispersed phase was prepared by simultaneously dissolving 25 mg of Apixaban, 100 mg of PLGA RG503H, 10 mg of PLA R20214, and 18.7 mg of glyceryl tridodecanoate in 1 mL of dichloromethane, and then the resultant was injected into a microfluidic chip (Dolomite, 3D focusing hydrophilic chip) at a flow rate of 0.01 mL/min. In particular, a 1% PVA solution was used the continuous phase, which was injected simultaneously with the dispersed phase at a flow rate of 0.1 mL/min, and liquid drops formed inside the microfluidic chips were obtained in the 1% PVA solution, which was stirred at 150 rpm. Subsequently, the thus-obtained microsphere liquid drops were observed under an optical microscope, and as a result, no drug precipitated from the microsphere liquid drops was observed (FIG. 13).

The microsphere liquid drops were further stirred at 35° C. for 2 hours to volatilize the organic solvent. After the organic solvent was removed, the microspheres were cured using a membrane filter, and then dried for 2 days by freeze-drying to obtain dried microspheres.

From these results, it was found that the Apixaban-loaded microspheres could only be prepared using the dispersed phase, to which the fatty acids or triglycerides were added, and the microfluidic method.

Experimental Example 6. Analysis of Drug Content in Apixaban-Loaded Microspheres In order to measure the drug content of the freeze-dried microspheres corresponding to Comparative Examples 1 and 2 prepared in Experimental Example 3, Comparative Example 3 prepared in Experimental Example 4, and Examples 1 to 7 prepared in Experimental Example 5, 1 mg of the finally freeze-dried microspheres were dissolved in in acetonitrile and filtered using a 0.45 μm PVDF syringe filter, and then subjected to quantitative analysis using a HPLC-UV device according to the conditions shown in Table 1 below.

TABLE 1

| Mobile phase | Water:ACN (60:40) |
|---|---|
| Column | YMC-Triart C18 column, C18 (150 × 4.0 mm ID), S-5 μm |
| Flow rate | 1 mL/min |
| Column temperature | 20° C. |
| Wavelength | 281 nm |
| Injection volume | 20 μL |

The content of the drug encapsulated in the microspheres was calculated by Equation (1) below.

Drug Content=Drug Concentration analyzed by HPLC (mg/mL)÷1 mg/mL×100(%)–(1)

The results of analyzing the Apixaban content in the microspheres calculated by the Equation (1) are shown in Table 2.

TABLE 2

| | Comparative Example 1 | Comparative Example 2 | Comparative Example 3 | Example 1 | Example 2 | Example 3 | Example 4 | Example 5 | Example 6 | Example 7 |
|---|---|---|---|---|---|---|---|---|---|---|
| Drug Content (%) | Measurement Not Possible | 0.57% | Measurement Not Possible | 18.40 | 17.61 | 18.36 | 20.41 | 18.60 | 18.65 | 18.92 |

Specifically, in the case of Comparative Examples 1 and 3, it was difficult to remove the drug crystals due to high contents of drugs crystals, and thus, it was not possible to measure the Apixaban content in the microspheres. In the case of Comparative Example 2, the microspheres obtained by removing the drug crystals as much as possible by washing three times with water using a 75 μm mesh sieve, followed by freeze-drying were used to measure the Apixaban content in the microspheres.

As a result, it was confirmed that the microspheres of Examples 1 to 7 prepared by the preparation method provided by the present disclosure could contained Apixaban in high contents in an amount of 15% to 20%.

From these results, it was found that even after freeze-drying, Apixaban was well encapsulated in the microspheres prepared by the preparation method provided by the present disclosure.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for preparing biocompatible polymer-based Apixaban-loaded microspheres for sustained release injectable formulation, the method comprising:

i) adding a fatty acid or triglyceride to a dispersed phase comprising Apixaban or a pharmaceutically acceptable salt thereof, a biocompatible polymer and a halogenated organic solvent; and ii) preparing biocompatible polymer-based Apixaban-loaded microspheres for sustained release injectable formulation using a microfluidic method, wherein the formation of Apixaban crystals is inhibited by addition of the fatty acid or triglyceride;

wherein the dispersed phase comprises Apixaban or the pharmaceutically acceptable salt thereof in an amount of 10% to 50% by weight relative to the biocompatible polymer, comprises the fatty acid or triglyceride in an amount of 50% by weight or less relative to the biocompatible polymer, and comprises the biocompatible polymer in an amount of 5 (w/v) % to 30 (w/v) % relative to the halogenated organic solvent, the biocompatible polymer is any one or more selected from the group consisting of polylactic-co-glycolic acid (PLGA), polylactic acid (PLA), and polycaprolactone (PCL), and the Apixaban-loaded microsphere comprises 5% to 30% by weight of Apixaban relative to the total weight of the Apixaban-loaded microsphere.

2. The method of claim 1, wherein the fatty acid is a C12-18 fatty acid having one or more carboxyl groups.

3. The method of claim 1, wherein the fatty acid is stearic acid or lauric acid.

4. The method of claim 1, wherein the triglyceride is formed with glycerol and three fatty acids having at least 10 carbon atoms and via an ester bond.

5. The method of claim 1, wherein the triglyceride is glyceryl tridodecanoate.

* * * * *